United States Patent
Park (10) Patent No.: US 7,955,867 B2
(45) Date of Patent: Jun. 7, 2011

(54) HIGH THROUGHPUT CELL-BASED ASSAYS, METHODS OF USE AND KITS

(75) Inventor: Jun Y. Park, Brookline, MA (US)

(73) Assignee: Millipore Corporation, Billerica, MA (US)

( * ) Notice: Subject to any disclaimer, the term of this patent is extended or adjusted under 35 U.S.C. 154(b) by 370 days.

(21) Appl. No.: 12/009,508

(22) Filed: Jan. 18, 2008

(65) Prior Publication Data
US 2009/0081698 A1 Mar. 26, 2009

Related U.S. Application Data (60) Provisional application No. 60/898,571, filed on Jan. 31, 2007.

(51) Int. Cl.
*C12M 3/00* (2006.01)
*C12N 5/02* (2006.01)
*G01N 33/537* (2006.01)

(52) U.S. Cl. ............ 436/538; 435/2; 435/7.2; 435/7.95; 435/40.5; 435/383; 435/395; 435/398; 435/401; 435/287.2; 435/288.4; 435/288.6; 436/518; 436/528; 436/172; 436/175; 436/177; 436/178

(58) Field of Classification Search ............... 435/2, 7.1, 435/7.2, 7.92, 374, 401, 287.2, 288.4, 288.6, 435/40.5, 383, 395, 398; 436/518, 523, 528, 436/538, 172, 175, 177, 178
See application file for complete search history.

(56) References Cited

U.S. PATENT DOCUMENTS

| | | | |
|---|---|---|---|
| 4,618,533 A | 10/1986 | Steuck | |
| 4,944,879 A | 7/1990 | Steuck | |
| 5,223,409 A | 6/1993 | Ladner | |
| 7,741,130 B2 * | 6/2010 | Lee et al. | 436/86 |
| 2001/0055776 A1 * | 12/2001 | Greenwalt | 435/7.1 |
| 2004/0091397 A1 * | 5/2004 | Picard | 422/99 |
| 2006/0019410 A1 | 1/2006 | St. Claire, III | |
| 2009/0170199 A1 * | 7/2009 | Raz et al. | 435/378 |

FOREIGN PATENT DOCUMENTS

| | | |
|---|---|---|
| WO | 95/24648 A1 | 9/1995 |
| WO | 2004/108286 A1 | 12/2004 |

OTHER PUBLICATIONS

Animal Cell Culture, R.I. Freshney, ed., p. 8, 13-30 and 38-39, 1986.
Extended European Search Report received for EP Patent Application No. 08250369.9, mailed on May 7, 2008, 5 pages.

* cited by examiner

*Primary Examiner* — Gail R Gabel (57) ABSTRACT

In the present invention cells are placed in a multiwell plate and grown. When the assay is to be performed, one uses gravity to wash away any unbound ligands rather than vacuum or centrifugation. The cells are then examined to detect the bound ligand. To perform the washing step(s) the plate is placed into a carrier plate having open wells in register with the wells of the filter plate or one may use a wicking device or an underdrain attached to the bottom of the filter plate. Sufficient wash liquid is added to allow for filtration by the effect of gravity to occur. Cells are retained within the wells at a rate of 4 times that of other rapid methods.

12 Claims, 10 Drawing Sheets

| MFI from flow cytometric analysis | | | | |
|---|---|---|---|---|
|  | 1 | 2 | 3 | 4 |
| A | 786 | 887 | 4.8 | 3.3 |
| B | 875 | 934 | 3.3 | 4.4 |
| C | 941 | 903 | 3.3 | 7.6 |
| D | 965 | 888 | 3.4 | 4.1 |
| E | 1053 | 914 | 4.2 | 3.9 |
| F | 957 | 878 | 3.2 | 3.9 |
| G | 937 | 880 | 6 | 4.4 |
| H | 933 | 906 | 4.9 | 3.7 |
| mean |  | 915 |  | 4.3 |
| s.d. |  | 56 |  | 1.1 |
| C.V. |  | 0.06 |  | 0.27 |
| Z' = |  | 0.81 |  |  |

HIGH THROUGHPUT CELL-BASED ASSAYS, METHODS OF USE AND KITS

CROSS-REFERENCED TO RELATED APPLICATIONS

This application claims the benefit of U.S. Provisional Application No. 60/898,571 filed Jan. 31, 2007 which is hereby incorporated by reference in it's entirety.

This invention relates to high throughput cell-based assays, methods of using such assays and kits for such assays. More particularly, it relates to a gravity based wash/filtration step for high throughput cell assays such as immunoassays.

BACKGROUND OF THE INVENTION

The use of various methods to detect the interactions between a cell and another entity (generally a drug or a drug candidate, a toxin, environmental contaminant, etc.) is well known in the art. A number of these cell based assay formats are widely available. These assays are used to detect the effect of a test compound on the expression of one or more marker molecules (generally proteins) of a cell.

Cell based assays generally measure a differentiative response requiring an immunoassay for a differentiation-specific marker molecule such as a protein on the cell wall or intracellular of the cell. Generally, at least a first ligand is added (first antibody or other entity) that binds to the marker molecule of the cell and either by itself or with a secondary ligand (such as a secondary antibody having a detectable marker) is capable of being detected, generally by fluorometry, colorometry or radioactivity.

Immunoassays are complicated by the need to remove unbound ligands before the detection step. Typically this has been accomplished with centrifugation wash protocols. The level of liquid after the addition of the one or more ligands is reduced and a wash buffer is added to the solution. This is then centrifuged and the supernatant removed leaving the cells in a small volume of liquid. The wash steps are often repeated 3-8 times in order to ensure the substantial removal of the unbound materials.

This is a time consuming process and limited in the number of tubes which can processed at any given time by one person. It also is not easily if at all automation compatible. Additionally, the amount withdrawn and where it is drawn from varies and leads to loss of cells either through decantation or due to stress or death due to lack of liquid (if too much is taken). Likewise, the number of washes must be kept high to ensure sufficient background reagent is removed so an accurate measurement can be made.

US 2001/0055776 A1 suggested the use of vacuum with a multiwell filter plate to provide a higher throughput format. The low vacuum is difficult to control and each well varies in its response to the low vacuum. This leads to inconsistent results between wells with some wells running dry while others retain too much fluid leading to false positive signals. More importantly, cell recovery is substantially low, albeit in some cases may permit an assay using remaining low number of cells.

The lack of a high throughput, high cell viability/retention assay is a significant bottleneck in the realization of proteonomics' full potential for drug discovery. The present invention provides such a solution.

SUMMARY OF THE INVENTION

In the present invention cells are placed in a multiwell plate and grown. When the assay is to be performed, one uses gravity to wash away any unbound ligands rather than vacuum or centrifugation. The cells are then examined to detect the bound ligand.

It is an object of the present invention to provide a process for the washing of cells used in a multiwell filter plate assay by gravity flow.

It is another object of the present invention to provide a process for the washing of cells used in a multiwell filter plate having a polycarbonate filter by gravity flow.

It is a further object of the present invention to provide a process for the washing of cells used in a multiwell filter plate having a hydrophilic polycarbonate filter by gravity flow.

It is another object of the present invention to provide a process for the washing of cells used in a multiwell filter plate having a hydrophilic polycarbonate filter with a pore size of about 3 microns by gravity flow.

It is an object of the present invention to provide a process for the washing of cells used in a multiwell filter plate assay by gravity flow to obtain high retention of cells.

It is an additional object of the present invention to provide a method of detecting a target specific reagent comprising the steps of:

a. selecting a cell having a selected target molecule located in a position selected from the group consisting of being on the cell wall or in the cell,
b. culturing the cell on a multiwell filter plate;
c. contacting the cell with a reagent comprising a ligand for a selected target molecule in or on the cell, the ligand being selected from the group consisting of ligands containing a detectable marker and ligands being capable of attaching to a secondary ligand that contains a detectable marker,
d. washing the cell with gravity flow at least one time to remove any reagent which is not bound to the selected target molecule of the cell to provide a washed cell; and
e. searching for the ligand to indicate the presence or absence of the target molecule (including the alterations in the functional state of the proteins such as phosphorylation of the proteins).

It is another object of the present invention to provide a primary and a secondary antibody as the ligand in the method.

It is a further object of the present invention to provide a primary and a secondary antibody as the ligand in the method and to detect the binding of the primary antibody to the target molecule through the use of fluorescence, chemiluminescence, colorometry or radioactive detection of the secondary antibody that is bound to the primary antibody.

It is an object of the present invention to provide a device for the gravity filtration of wash fluids and unbound reagents formed of a filter plate having two or more wells, the bottom of each well being covered by a porous membrane; a carrier plate having wells equal in number and in register with the wells of the filter plate, the carrier wells having open tops and bottoms; and a collection tray.

It is a further object of the present invention to provide a filter plate with a hydrophilic membrane having a pore size of from about 1 to about 5 microns, preferably about 3 microns.

It is an additional object of the present invention to provide a carrier plate having wells the inner diameter of which is at least slightly larger than the outer diameter of the wells of the filter plate with which it interacts.

It is another object of the present invention to provide a filter plate with a hydrophilic membrane and a carrier plate having wells the inner surfaces of which have been rendered hydrophilic.

It is an object of the present invention to provide a kit formed of a multiwell filter plate, a plate carrier, a waste collector for use in the washing of cells by gravity flow.

It is another object of the present invention to provide a kit formed of a multiwell filter plate having a hydrophilic membrane, a plate carrier, a waste/reagent collector for use in the washing of cells by gravity flow.

It is an object of the present invention to provide a kit formed of a multiwell filter plate having a hydrophilic polycarbonate membrane with a pore size of about 3 microns, a plate carrier, a waste/reagent collector for use in the washing of cells by gravity flow, a first antibody capable of binding to the marker protein and a second antibody capable of binding to the first antibody, wherein the second antibody has an entity that is capable of being detected.

It is an object of the present invention to provide a kit with a secondary antibody that is capable of being detected by fluorescence, colorometry or radioactivity.

It is an object of the present invention to provide a kit with a secondary antibody that is capable of being detected by flow cytometry.

IN THE DRAWINGS OF THE INVENTION

DETAILED DESCRIPTION OF THE INVENTION

The invention is a rapid-throughput cell-based assay and a related kit and method of use that can be used, for example, to screen test compounds for their effect on cell growth and differentiation as indicated by expression of marker proteins of a cell. The components of the invention are described in detail below. Briefly, cells are cultured on a filter plate. The filter plate comprises a low background phosphorescence material with pores which permit cells to be cultured on the filter plate and to be washed in situ. Loss of cells is minimized by using gravity filtration for wash steps.

Cells on the plate are contacted with a reagent which comprises a ligand which specifically binds to the marker molecule of the cell, typically a protein and to a detectable agent. The detectable agent can be a lanthanide ion chelated to a chelating agent, and the chelating agent is bound to the ligand or it may be any of the commercially available antibodies and the like that have a detectable entity formed or attached to it. Cell culture medium can be removed, if desired, before the cells are contacted with the reagent. Optionally, the reagent can be added directly to the cell culture supernatant. Direct addition avoids additional wash steps and further increases the high throughput nature of the assay.

After washing the cells to remove unbound reagent, detection, such as by fluorescence, chemiluminescence, radioactivity, or colorometry, associated with the detectable agent can be measured. The detection of the entity indicates binding of the ligand to the marker molecule and therefore can be used to detect the presence of the marker molecule. In one embodiment using fluorescence, the high background fluorescence characteristic of cell-based assays can be minimized using time-resolved fluorescence measurement of the fluorescence.

In one embodiment of the invention, the ligand is a single primary antibody, which decreases processing time relative to assays which use both primary and secondary antibodies. Alternatively, two ligands, such as a primary and a secondary antibody, or a first ligand coupled to biotin and a second ligand comprising avidin or streptavidin, can be used.

The method of the invention can be used, inter alia, to monitor differentiation of a cell, to assess the viability of the cell, or to screen test compounds for various effects on marker protein expression. Because marker protein detection can be carried out using the same filter plate on which the cells are cultured, the method is easily adapted for use in high throughput screening formats, thus relieving a significant bottleneck in the screening of test compounds for desired or undesired effects in vivo.

The invention also provides a test kit for use in the screening and detection methods of the invention. The kit comprises a ligand for a marker molecule, a detectable entity either as part of the ligand for the marker molecule or a secondary ligand that attaches only to the first ligand, a filter plate suitable for culturing cells, a carrier plate for holding the filter plate and a filtrate collection plate. The filter plate in the kit preferably has a low background phosphorescence material with pores of a size that permit cells cultured on the filter plate to be washed in situ by gravity flow. Optionally, the test kit also includes a cell which is capable of expressing a marker protein. If desired, instructions for various methods of the invention can be provided in the test kit.

Cells which can be used in the detection and screening methods of the invention are not limited to any particular type but will generally be mammalian, preferably human, cells. Such cells include cultures of primary cells as well as neoplastic or normal cell lines. Single or multiple cells can be cultured, e.g., maintained in vitro. In one embodiment, the cell is a progenitor cell which is capable of further differentiation, such as a stem cell of the bone, testis, or stratified squamous epithelium, an embryonic stem cell, a neural progenitor cell, a glial progenitor cell, or a hematopoietic progenitor cell, including a granulocytic, monocytic, erythroid, megakaryocytic, myeloid, and lymphoid stem cell.

Any medium in which a particular cell type can be cultured for expression of the marker molecule to be detected can be used in the method of the invention. The selection of an appropriate culture medium for a given cell type, as well as other culture conditions such as temperature and percent of carbon dioxide, is well within the skill of those in the art (see, for example, ANIMAL CELL CULTURE, R. I. Freshney, ed., 1986).

Marker molecules which can be detected according to the invention are typically proteins and can be determined by the nature of the cell being cultured and include both cell-surface and intracellular proteins. The invention is not limited to the use of any particular marker proteins. If an intracellular marker protein is to be detected, cells are preferably fixed and permeabilized, as is known in the art, before incubation with the first ligand or with the second ligand containing a detectable entity. Intracellular marker proteins which can be detected according to the invention include, but are not limited to, hemoglobin A, cytokeratins, cytokines (e.g., IL-4, IFN$_\gamma$), actin, signal transduction molecules, tartrate-resistant acid phosphatase (a marker for osteoblast differentiation), von Willebrand factor, and neuronal progenitor differentiation markers, such as GFAP, MAP2, beta tubulin III, and nestin.

Marker proteins which can be detected to assess the toxicity of various test compounds are those which are present in many cell types, and include proteins such as aldehyde dehydrogenase (ALDH), collagen, glyceraldehyde 3-phosphate dehydrogenase, elongation factor 1 alpha, and gamma actin. Marker proteins which can be detected to assess the effect of test compounds on the cell cycle include various microtubule and microfilament proteins. Other marker proteins, which are cell type- or cell stage-specific, can be detected to assess the effect of test compounds on cell differentiation. These marker proteins include, for example, hematopoietic markers, such as hemoglobin A, glycophorin A, gpIIbIIIa, the erythropoietin receptor, CD11b, CD19, CD33, CD34, CD36, CD41, MO1, OKT3, OKT4, OKT8, OKT11, OKT16, OKM1, OKM5, Leu7, Leu9, Leu M1, and Leu M3; neuron-specific marker proteins, such as acetylcholinesterase, glial-specific marker proteins, such as glial fibrillary acidic protein (GFAP) and myelin basic protein; and other proteins found only in specialized cells, such as human milk fat globule antigen (HMFG), keratins, and crystallins.

Optionally, two or more marker proteins can be detected in the same cell or cell culture, either simultaneously or sequentially, using ligands which specifically bind to each of the marker proteins. For simultaneous detection, for example, different ligands can be used having distinguishable excitation and/or emission maxima for their respective detectable entity.

Typically, a ligand which specifically binds to a marker protein binds to the marker protein with an affinity which is at least about 2- to 3-fold, preferably 5- to 10-fold, even more preferably 20-fold higher than the affinity with which the ligand binds to other proteins when used in an appropriate binding assay. If the ligand is an antibody, for example, appropriate assays include immunochemical assays, such as a Western blot radioimmunoassays, or immunocytochemical assays. Preferably, an antibody which specifically binds to a marker protein does not detect other proteins in immunochemical assays and can immunoprecipitate the marker protein from solution. Binding affinity of a ligand to a receptor, or of a ligand which is a receptor to its own ligand, can be assayed by radioimmunoassay, fluorescence quenching, or other suitable assays known in the art. Antibodies, such as monoclonal or polyclonal antibodies, single-chain antibodies, Fab fragments, (Fab') 2 fragments, and the like, are conveniently used in the method of the invention. The term "antibody" as used in the specification and claims is intended to embrace all of these alternatives.

In another embodiment of the invention, a first ligand, such as a primary antibody or a biotin-, avidin-, or streptavidin-labeled ligand, is bound to the marker protein. A second ligand conjugated to a lanthanide chelate or other detectable entity is then bound to the first ligand. For example, the first ligand can be a primary antibody and the second ligand can be a secondary antibody. Many suitable primary-secondary antibody pairs are well known in the art and can be used in this embodiment of the invention. Alternatively, the first ligand can comprise a biotin moiety and the second ligand can comprise avidin or streptavidin. If desired, the first ligand can comprise avidin or streptavidin and the second ligand can comprise biotin. Other specific binding pairs also can be used, as is known in the art.

Detection can be either qualitative or quantitative. Fluorescence preferably is detected by a method using time delay, which reduces or eliminates the contribution of non-specific background fluorescence to the detected signal. A preferred method of detection is time-resolved fluorometry. Use of radioactive entities may also be used as well as the use of various colorometric entities.

Washing steps necessary to remove unbound ligand contribute to the labor-intensive character of immunoassays and decrease their throughput. In addition, loss of cells during washes or during the transfer of a cell culture is always an important concern. In the current assay, this problem has been essentially eliminated by use of porous filter plates on which the cells are cultured and gravity washed in situ. The average pore size of the filter plate is sufficient to permit culture medium, wash fluid, and unbound ligands, etc. to pass through under the effects of gravity while retaining the cultured cells. In the absence of sufficient volume of liquid in a well, the average pore size is such that surface tension effects are sufficient for the filter to act as a culture plate for cells ranging in size, for example, from 5 µm to 30 µm in diameter. Filter plates useful in the inventive methods typically have average pore sizes between 0.45 and 5 µm, preferably between about 1.0 and 5.0 µm, and even more preferably about 3.0 microns.

Thus, the ideal filter plate for use in the inventive methods is cell culture compatible and is constructed, at least in the surface, of a membrane material that has low background phosphorescence and low non-specific protein binding properties. An acceptably low background phosphorescence is preferably about 10,000 counts or less, more preferably about 5000 counts or less, even more preferably about 500 counts or less, as measured, for example, using a spectrofluorimeter (e.g. Victor or Victor$^2$™ from EG&G Wallac, or the equivalent). Additionally, the plates should have an acceptably high gravity filtration rate and come with both top and bottom covers to minimize evaporation. Preferably, the plates are available in the well-known 96- or 384-well formats and have a membrane material that is transparent to allow viewing of cells.

Suitable materials for use in filter plates in this invention can be investigated using routine screening techniques. Materials having low phosphorescence, low non-specific protein binding properties, properties which are compatible with cell culture requirements, and which can form pores with average diameters which permit cells to be both cultured in the filter plate and washed in situ, such as polycarbonate, should generally be suitable.

Numerous commercially available filter plates were examined to determine their suitability for use in the assay of this invention. The MultiScreen® PCF filter plate available from Millipore Corporation of Billerica, Mass. has been determined to exhibit background phosphorescence of approximately 5,000 counts, with excitation at 340 nm and emission at 615 nm. An even more preferred filter plate is the black polycarbonate membrane plate designated as the "MultiScreen® Fluoresence" plate available from Millipore Corporation of Billerica, Mass.

Test compounds to be screened for the ability to affect marker molecule expression can be any pharmacologic agents already known in the art or can be compounds previously unknown to have any pharmacological activity. Test substances can be naturally occurring or synthesized in the laboratory. They can be isolated from microorganisms, animals, or plants, or can be produced recombinantly or synthesized by chemical methods known in the art.

Because the present invention is conducive to high throughput screening, test compounds typically are obtained from compound libraries. Methods of generating combinatorial libraries of test compounds are known in the art and include, but are not limited to, formation of "biological libraries," spatially addressable parallel solid phase or solution phase libraries, synthetic library methods requiring deconvolution, the "one-bead one-compound" library method, and synthetic library methods using affinity chromatography selection (15-21). The biological library approach is limited to polypeptide libraries, while the other four approaches are applicable to polypeptide, non-peptide oligomer or small molecule libraries of compounds (13). The present invention, however, is in no way limited to the method for generating, or source of potential test compounds.

Test compounds can be presented to cells, for example, in solution, on beads, plasmids, or phage, see U.S. Pat. No. 5,223,409, incorporated herein by reference. Optionally, the degree to which the test compound affects expression of the marker molecule can be quantitated. For example, fluorescence associated with a lanthanide ion can be quantitated in the presence of the test compound (first fluorescence), and fluorescence associated with the lanthanide ion in the absence of the test compound (second fluorescence) each can be measured. Subtraction of the second fluorescence from the first fluorescence provides the difference between the two fluorescences and, therefore, the degree to which the test compound affects expression of the marker molecule in this instance a protein. Preferably, the first and second fluorescences are associated with the same type of detectable entity in this case lanthanide ion (e.g., Europium), so that an effective comparison can be made.

Figure 1:
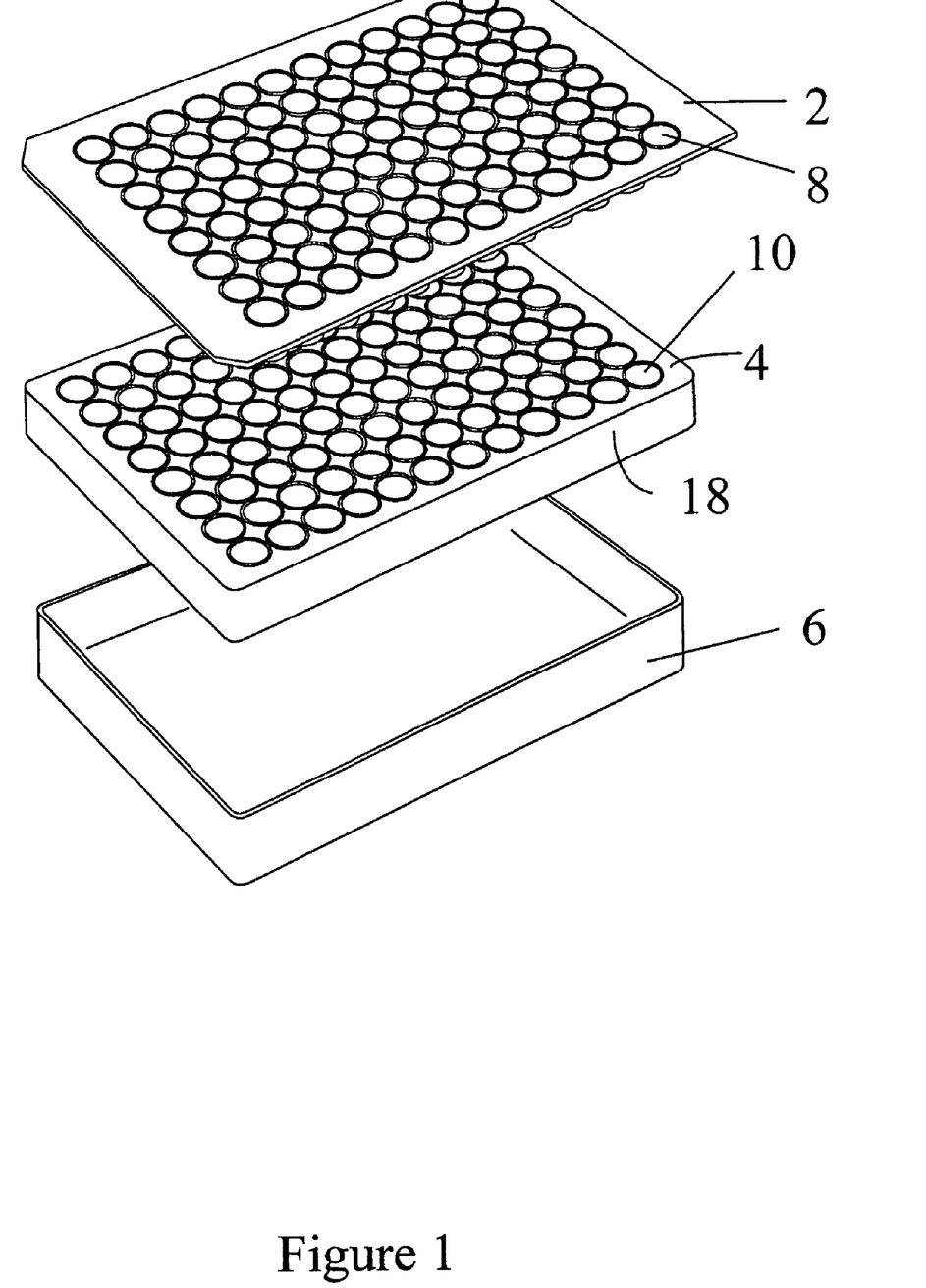
FIG. 1 shows an embodiment of the device of the present invention in exploded perspective view.
Figure 2:
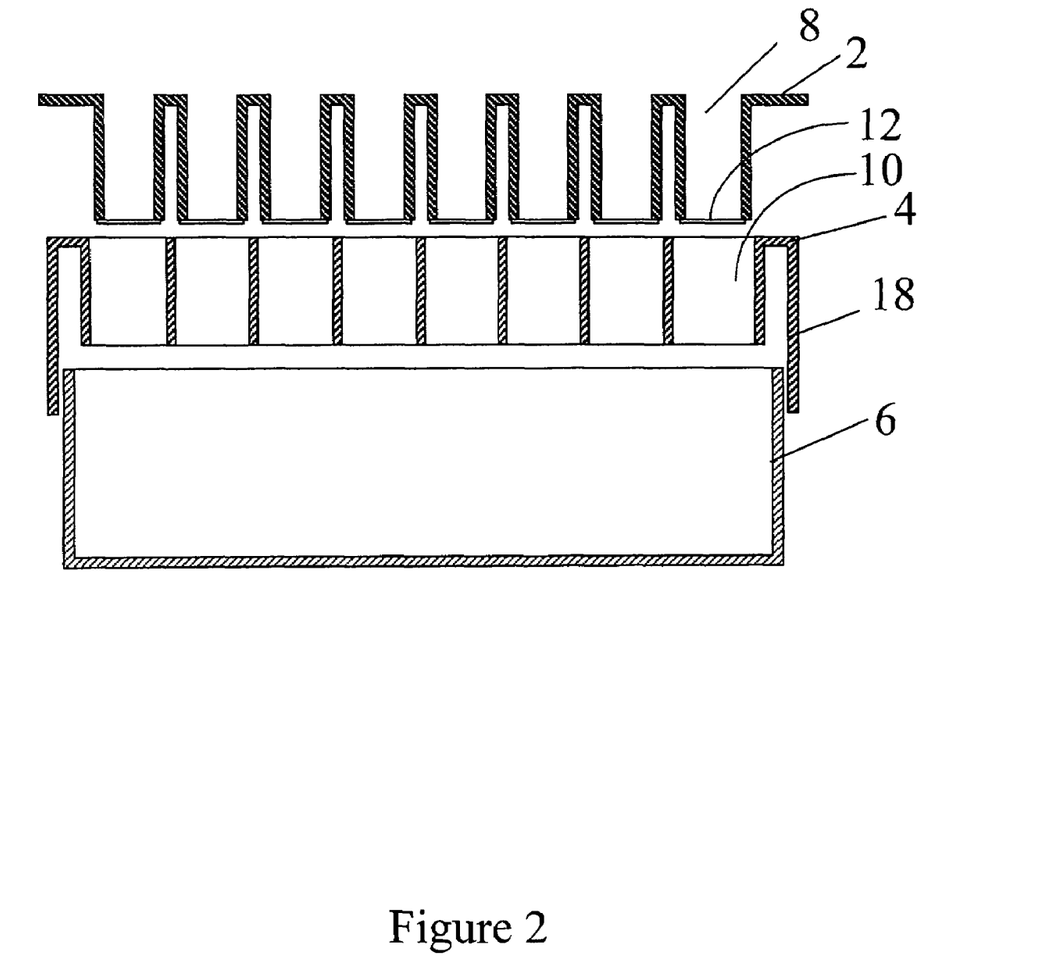
FIG. 2 shows an embodiment of the device of the present invention in exploded cross sectional view.

The device of the present invention preferably comprises three components as shown in FIG. 1, a multiwell filter plate 2, a carrier plate 4 and a filtrate collection tray 6 or manifold. The multiwell filter plate 2 has a series of two or more wells 8 extending downward from a substantially planar upper surface 10. The number of wells can vary depending upon volume required and the size of the plate 2. Typically they range from 8, 24, 48, 96 or 384 wells per plate 2.

Each well 8 has a porous filter 12 attached to its lower portion selectively sealing off the well 8. The carrier plate 4 has a series of open wells 10 extending through it. The wells 10 have an inner diameter that is slightly greater than the outer diameter of the wells 8 of the multiwell plate 2. The wells 10 are in equal number and in register with the wells 8 of the multiwell plate 2.

In one embodiment, the inner diameter of the wells 10 of the carrier plate 4 are sufficiently large such that there is an air gap (~0.2 to 0.5 millimeter) between the inner diameter of the carrier wells 10 and the plate wells 8 when the multiwell plate 2 is inserted into the carrier plate 4.

In another embodiment, the inner diameter of the wells 10 of the carrier plate 4 are either inherently hydrophilic such as through the selection of a hydrophilic polymer or rendered hydrophilic through the use of a coating. Alternatively or additionally, the open bottoms of the wells 10 of the carrier plate may be tapered to form collectors or spouts 14 for liquid that passes through it. Those limit cross contamination and splashing during washing and other liquid steps of the present process.

Figure 5:
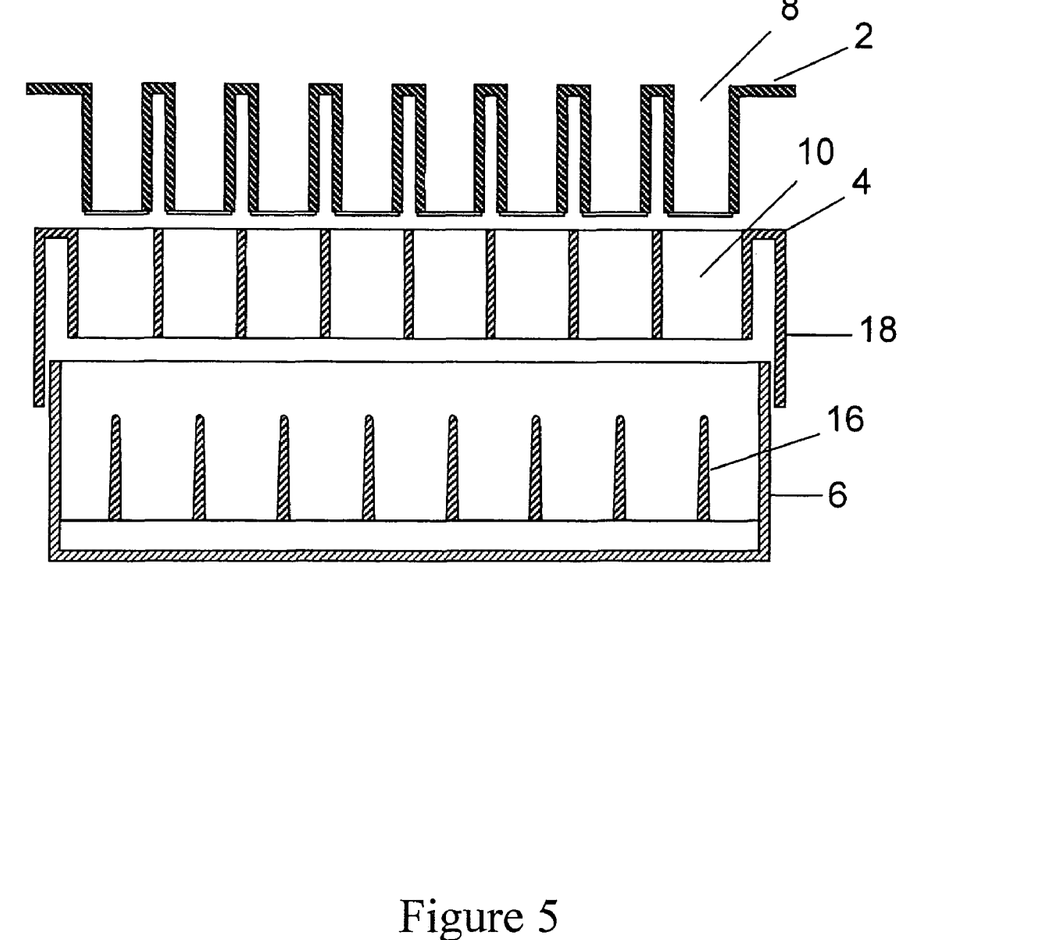
FIG. 5 show another embodiment in cross sectional view.

In a further embodiment, the tray 6 may contain a wicking device 16 such as an absorbent pad or set of ribs (shown in FIG. 5) which sit in the tray below the wells 8 of the multiwell plate 2. This wicking device is used to pull the liquid drops formed on the outer bottom surface of the filters of the wells 8 more quickly and completely into the filtrate collection tray 6. The wick is spaced apart from the bottom of the filter. Several such wicking devices are shown in U.S. Pat. No. 6,989,099 and incorporated herein by reference in its entirety.

The membrane may be a microporous membrane formed of a polymer selected from olefins such as polyethylene including ultrahigh molecular weight polyethylene, polypropylene, EVA copolymers and alpha olefins, metallocene olefinic polymers, polycarbonate, vinyl copolymers such as PVC, polyamides such as nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof.

The membrane selected depends upon the size of the cells used in the application, desired flow characteristics and the like.

Preferably the membrane is selected from polycarbonate, PVDF, a nylon (such as Nylon 66) or polyethersulfone (PES).

Preferably, the membrane is hydrophilic either inherently or through the addition of a second polymer blended into the base polymer (such as PVP with polysulfone) or the use of coatings crosslinked, grafted to or otherwise irreversibly coated over the membrane as is well known in the art see U.S. Pat. No. 4,618,533 and U.S. Pat. No. 4,944,879. Preferred membranes are polycarbonate, PVDF or PES with a hydrophilic coating applied as by U.S. Pat. No. 4,618,533. Such membranes are available from a variety of sources including Millipore Corporation of Billerica Mass. under the brand names of Durapore® hydrophilic PVDF membranes, Millipore Express® or Millipore Express® Plus hydrophilic PES membranes or Isopore™ hydrophilic polycarbonate membranes.

The pore size should be small enough so as to prevent the cells from being pulled into or through the membrane pores, but large enough to allow for good flow characteristics and its optimal size will depend on the type of cells. Preferably it is from about 0.45 micron to about 5 microns in diameter, more preferably between about 1 micron and about 3.5 microns and most preferably between about 2 and 3 microns. Most cells have a diameter of greater than 7 microns (with an exception of platelets, 3 microns, and red blood cells, 5 microns) and the use of a membrane having a pore size of about 3 microns prevents the cells from passing through while providing an acceptable flow rate.

Symmetrical or asymmetrical membranes may be used. Symmetrical membranes have a substantially consistent pore size through their thickness (generally less than 2 times difference in pore sizes from a first face to the second opposite face of the membrane). Asymmetrical membrane have a pore size that varies at least a portion of the way through the thickness and often all the way through the thickness of the membrane (generally 2 to 1000 times difference in pore sizes from a first face to the second opposite face of the membrane). Symmetrical membranes are preferred in one embodiment. Asymmetric membranes with the tight side facing the cells are preferred in another embodiment. Asymmetric membranes with the open side pore size being less than about 5 microns and facing the cells are preferred in another embodiment of the present invention.

The device of the present invention may also have guide members on the multiwell plate 2 carrier plate 4 and/or collection plate 6 to hold the various components together in alignment. As shown in this example a rim 18 on the carrier plate 4 is used to center and align it over the collection plate 6. The multiwell plate 2 is centered on the carrier plate 4 by insertion of the multiwell plate's wells 8 into the wells 10 of the carrier 4.

If desired, alignment pins, knocked off corners on the plates (2, 4) and other such well-known devices may also be used to ensure that the plates are assembled in only one direction if desired.

Figure 3:
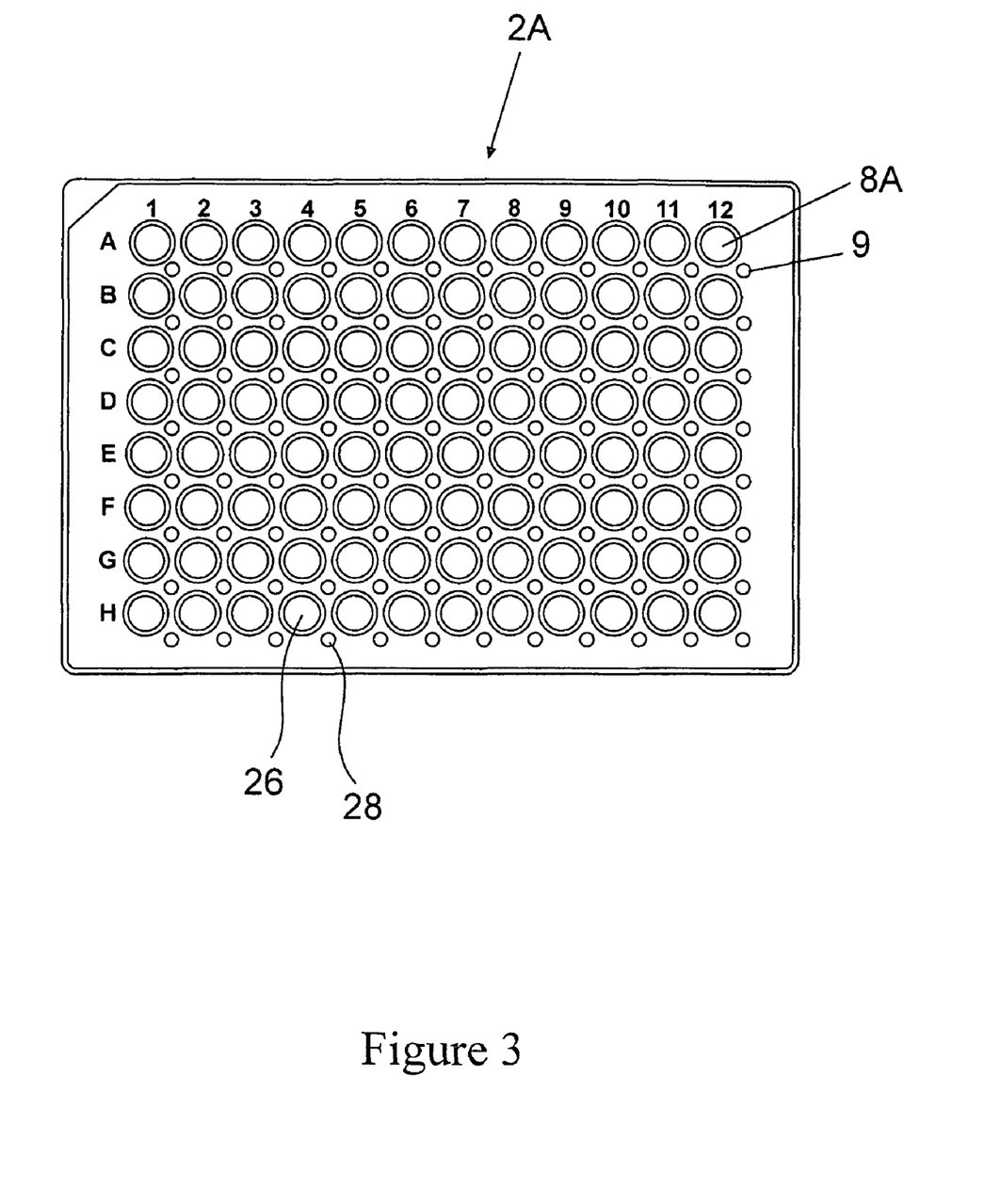
FIG. 3 shows an alternative embodiment of the filter plate used in the device of the present invention in top down view.
Figure 4:
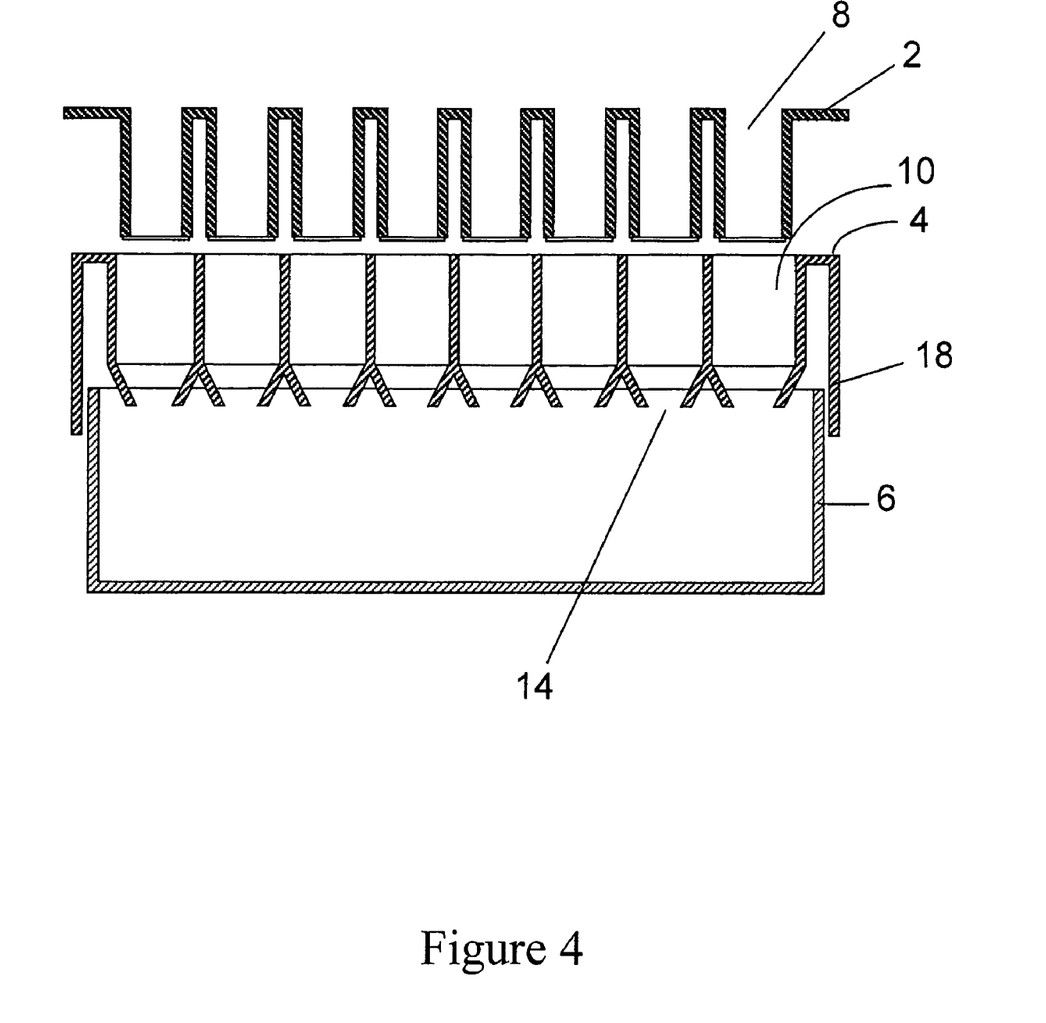
FIG. 4 shows a wicking device used in the device of the present invention in cross sectional view.

As shown in FIG. 3, the multiwell plate 2A may be a plate designed specifically for growing cells. Such a plate is available from Millipore Corporation of Billerica, Mass. and sold as the MultiScreen® CaCo$_2$ cell plate. It contains wells 8A and arranged adjacent each well 8A is a port 9 which provides access to a closed well (not shown) which contains the media in which the cells grow.

The device of the present invention is assembled so that the wells 8 or 8A of the multiwell plate 2 or 2A are at least partially inserted into the wells 10 of the carrier plate 6. The carrier plate 4 is either then fit and affixed to the collection plate 6 or it was affixed before insertion of the multiwell plate 2 or 2A.

One process of the present invention (shown in FIG. 6) is in a first step 100 to have first grown cells in the multiwell plate 2 or 2A that is placed in a cell culture tray (not shown) until cells have reached a desired density. In the second step 102, the multiwell plate 2 or 2A is then removed from the culture tray and placed into the carrier plate 4 as described above.

Figure 6:
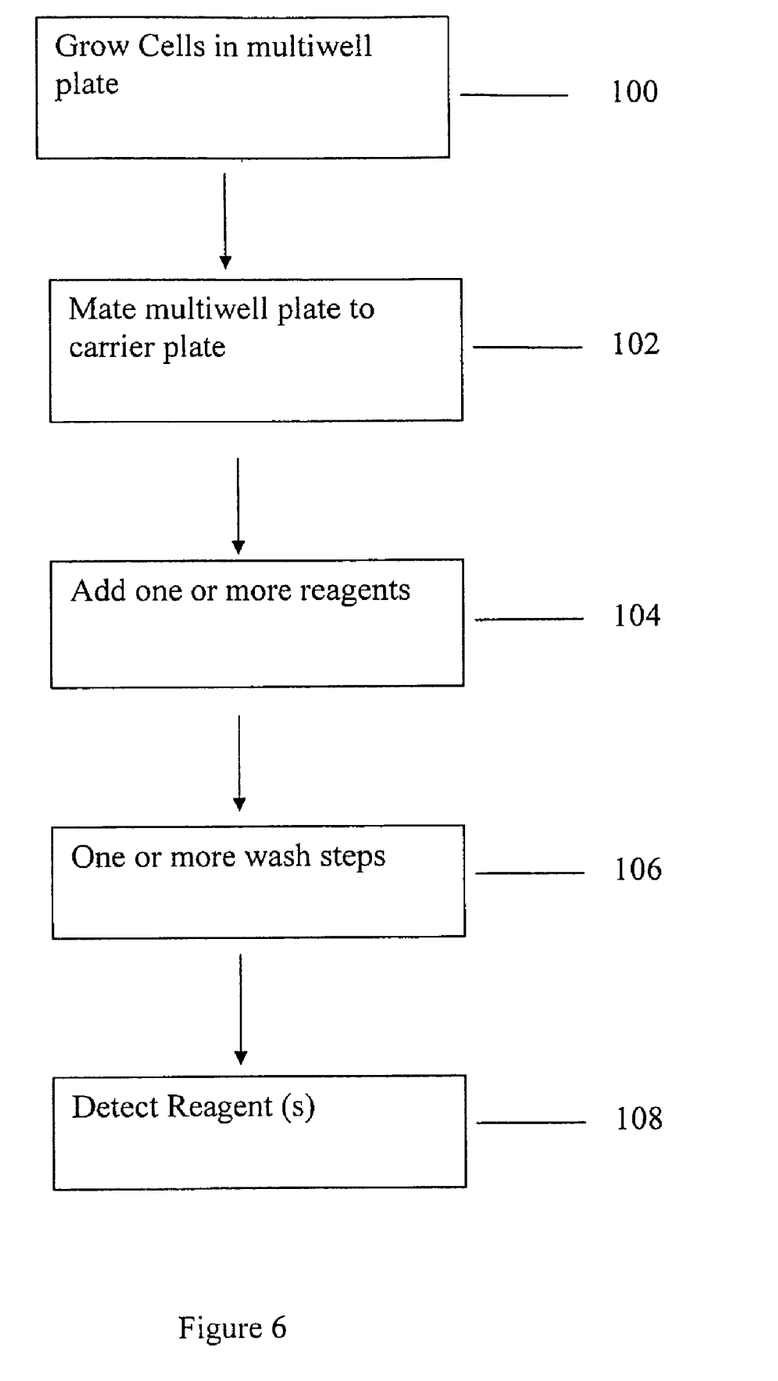
FIG. 6 shows a method according to the present invention in block diagram format.

The carrier plate 4 has either already been affixed to the collection plate 6 or if not, then it along with the mated multiwell plate 2 are affixed on top of the collection plate.

Each well 8 will contain a lower level of liquid that support the cells viability. However, the level is insufficient to overcome the resistance of the filter pores to flow.

Depending upon the detection system used, at least one reagent is added to one or more wells and allowed to incubate so that it may interact with the cell or marker molecule expressed by the cell in the third step 104. Unbound reagent is then washed one or more times by simply adding a wash buffer (such as water, buffered water, saline solution and the like) to a volume that creates a head height sufficient to allow the liquid to penetrate the pores of the filter and flow out of the well under the influence of gravity through the carrier plate 10 and into the collection plate 6 in the fourth step 106.

If desired, additional reagents, such as secondary antibodies, can be added sequentially with one or more washes being used between the addition(s) as desired to remove any unbound material, thus reducing background noise typically caused by the unbound materials being present during the detection step.

The presence/absence and its desired quantity of the marker molecule is then detected in the last step 108. Typical detector reagents include but are not limited to antibodies, dyes, ligands, chemiluminescent chemicals, radioactive isotopes and compounds and the like. They are generally detected using methods such as fluorometry, flow cytometry, colorometry, radio activity, optical density measurement and the like.

Figure 7:
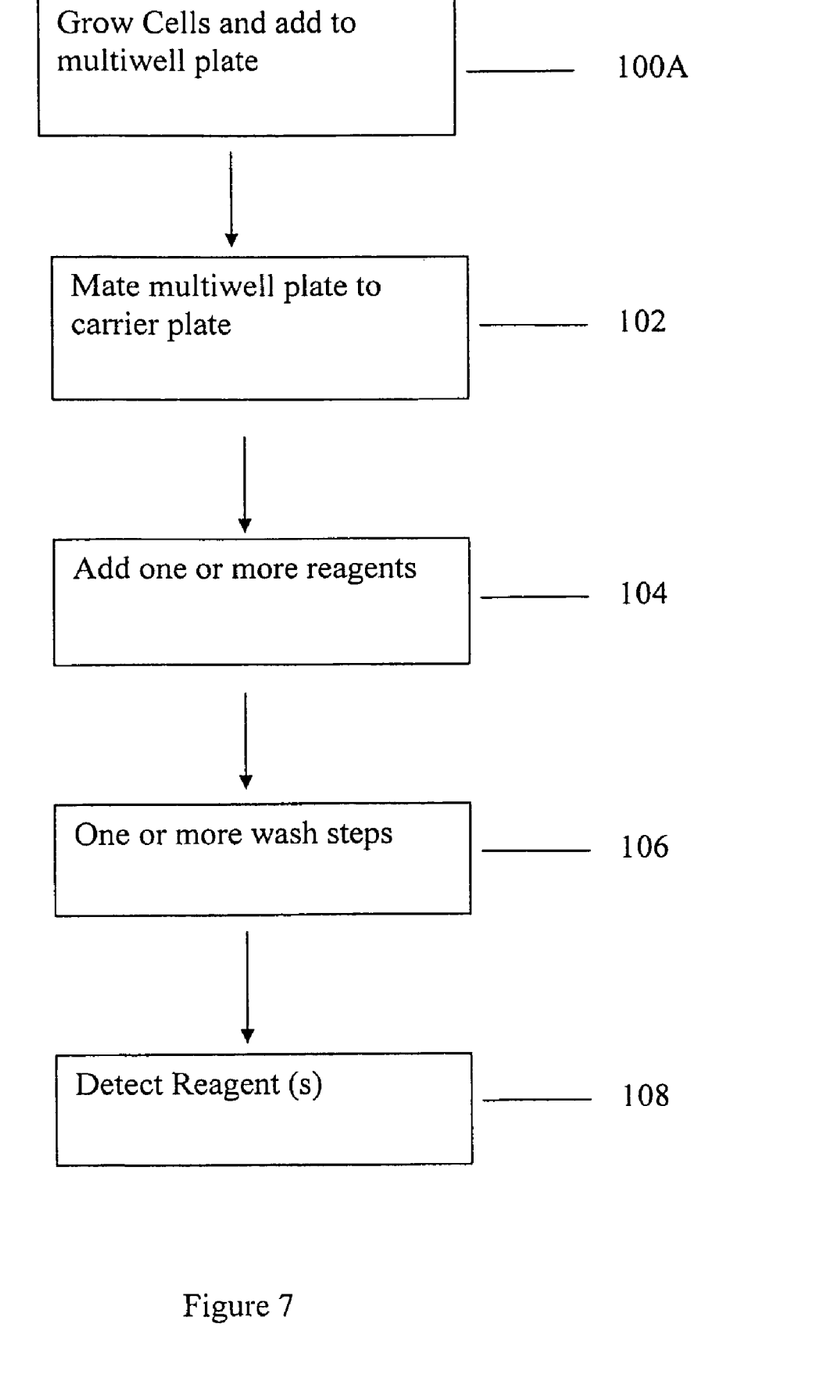
FIG. 7 shows a second method according to the present invention in block diagram format.

In another process according to the present invention, the cells are grown elsewhere in a first step 100A and added to the wells 8 at the multiwell plate 2. From there, the process is substantially identical to that described above.

In either process, but especially with the process using cells added to the wells 8 of the multiwell plate 2, at least the carrier plate 4 is pre-wet before use. Preferably the filter of the multiwell plate 2 is also pre-wet to enhance liquid flow when desired. This can be accomplished by either pre-wetting either or both components separately or when both are to be pre-wet by pre-wetting then simultaneously as the assembled subunit.

Buffered balanced salt solutions and the like can be used to pre-wet the filters and the surfaces of the carrier plate 4.

It has been found that when carrier plates are rendered hydrophilic, such as by using plasma treatment, the time necessary to have gravity flow the liquid through the system is cut in half. A typical system generally will flush in from about 2 to about 5 minutes depending upon various parameters such as liquids used, its volume in the well, the density of the cells in the well. The same system having hydrophilic carrier plate flushes in about 1 to 2 minutes.

As the system is gravity driven, the amount of liquid added is important as head height or the pressure of the volume of the liquid itself drives the filtration process.

Generally, it has been found that a well of a 96 well plate using a hydrophilic polycarbonate 3 micron pore size membrane will hold about 100 μL of liquid without any flow. The addition of wash solution creates sufficient head height to cause gravity-based flow through the system at an acceptable rate. Typically, one uses from about 100 to 250 μL of additional wash fluid, depending on the well volume and speed and thoroughness desired for washing.

In some instances, the use of vibration or rocking may help speed the process, although it is not required.

Once the level of liquid reaches a low enough volume, filtration is shut off as the liquid is no longer able to overcome the inherent resistance against flow. This is an interesting and helpful feature of the present invention as it prevents the wells from drying out as can occur with vacuum filtration or centrifugation. Additionally, as the force (gravity) is gentle on the cells and the liquid, there is little cell damage or lysis and little or no foaming of the liquid which can obscure detection. Lastly, cells lost due to the filtration is minimized as compared to either vacuum certrifugation, whose forces are sufficiently high so as to forcibly pull cells into and/or through the filter.

The present invention can be used with free floating (suspension) cells as well as adherent cells. If adherent cells are used, it preferred that they be grown on a carrier such as microcarrier beads, non-wovens or other scaffolding systems so that the pathways to the pores in the plate are still accessible to the fluid. Alternatively one can grow the adherent cells at less than optimal densities or trypsinize the cells before processing.

The plates, kit and process of the present invention can be easily automated with any commercial liquid handler. All one needs to do is to regulate the amount of liquid added in each step and/or add a pre-wetting step as described above so that one only achieves flow when desired and to regulate the time between the steps as well as the number of steps to ensure that sufficient time is expended for each wash step to allow for adequate removal of the unbound materials.

EXAMPLE 1

Gravity based filtration of cells for cell-based assays was conducted using the following protocol:

Jurkat cells (T-lymphoblastic cell line) were cultured on two 96 well filter plates containing a 3 micron pore size hydrophilic polycarbonate filter, (100 μL final volume, in complete media containing 10% FCS (fetal bovine serum): the assay contained 100,000 cells per well.

On the day of assay, the bottom of each filter plate was pre-wetted using PBS, and placed into a carrier plate.

The assembled devices were then placed onto a liquid filtrate collector.

Cells were washed by adding 200 μl of wash buffer (PBS containing 1% FBS or BSA) per well.

Once the wash buffer was added to the wells, the liquid started to drain out of the wells forming droplets and dropped into the collector via gravity (while cells were retained inside of the wells). Drained out liquid was collected in the liquid collector.

After about 2 minutes equilibrium was reached where no or very little liquid would drain out from the wells. There was about 100 μL of liquid remaining in the wells.

An additional 200 μL of wash buffer was added.

In one plate, cells were then treated with a CD45 specific antibody (anti-CD45) (Invention Plate). The other plate (Control Plate) was treated with a control (isotope) antibody (~3 μg/mL final concentration for antibodies in both instances) and incubated for 30 minutes. Liquid inside of the wells remained and the cells did not dry out during the incubation.

Excess unbound antibodies were removed by washing as indicated above in steps 3 and 4 three times.

A secondary antibody, Alexa 488 conjugated antibody (available from Invitrogen Corporation) was added to the wells of each plate and incubated for 30 minutes, and then washed three times as indicated above in steps 3 and 4.

Prepared cell samples were analyzed using a Guava benchtop flow cytometer (fluorescent detection).

Figure 8:
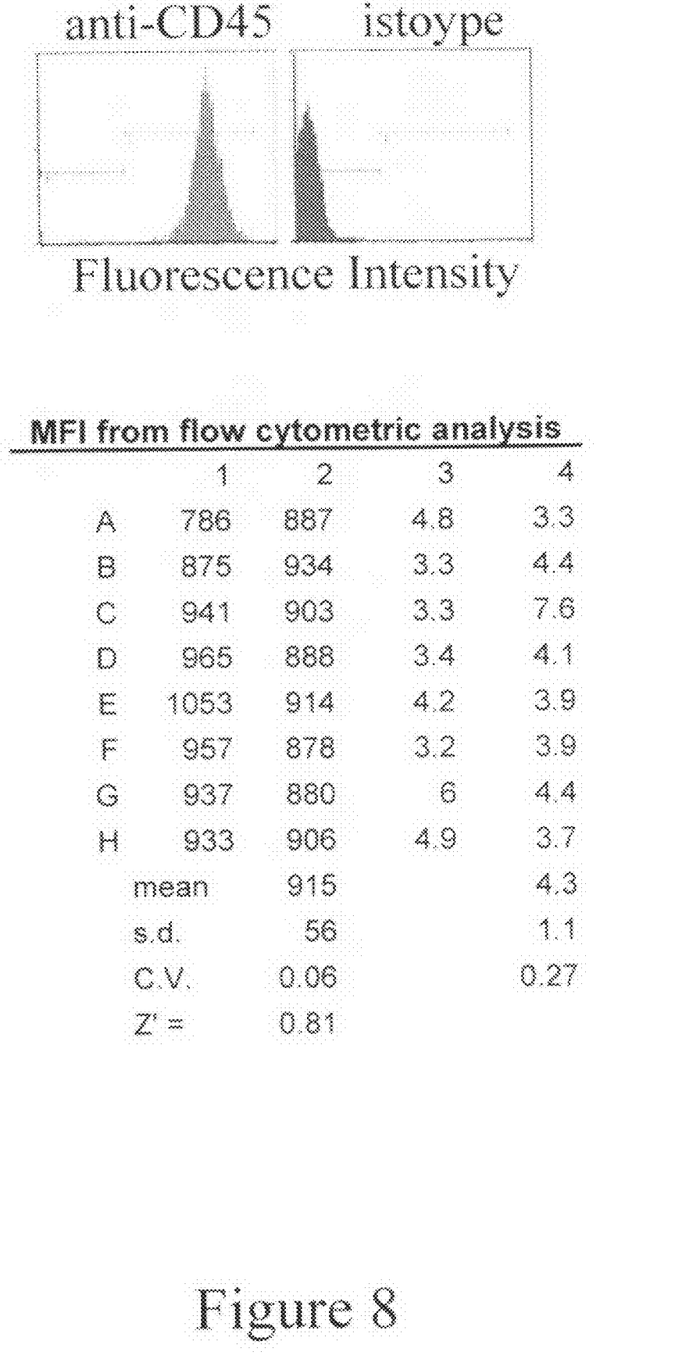
FIG. 8 shows data from Example 1.

As shown in FIG. 8, the histograms show clear populations of cells stained with the antiCD45 antibody (left side panel). Control cells stained only with the isotope antibody are shown in the right panel. Tabulated summary of the fluorescence measurement is shown as well in FIG. 8.

EXAMPLE 2

In this example, cells were tested according the protocol of Example 1 and compared to the washing of cells prepared by the vacuum process of US 2001/0055776A1.

For the method of the present invention the cells were washed 6 times.

For the vacuum method, a 0.4 micron pore size polycarbonate filter plate was used and washed 3 times at about 5 inches of mercury as described by the referenced application above.

Remaining cells in both plates were measured by ATP based luminescent measurement.

Figure 9:
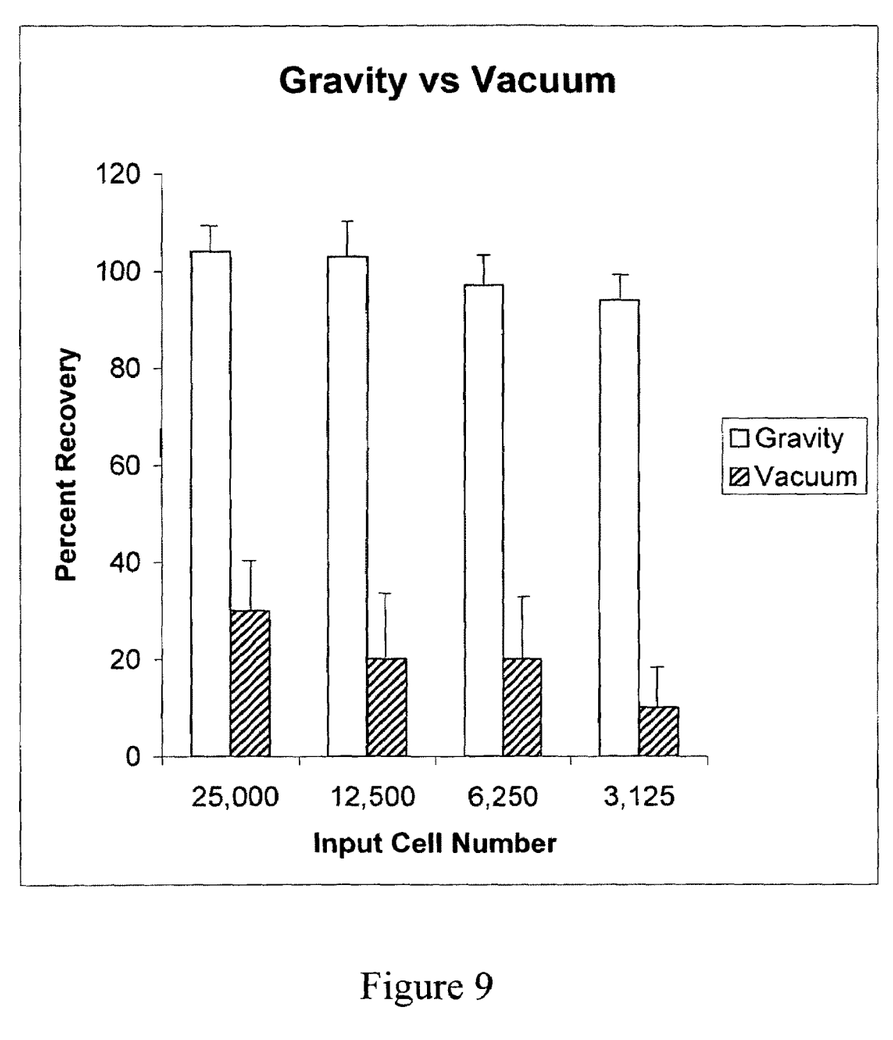
FIG. 9 shows data from Example 2.

As shown in FIG. 9, the number of cells input into each well is listed below the X axis of the graph. The percentage of recovery is shown respectively for the method and device according to the present invention and that of the prior art. Line bars extending from the solid bars represent the variation that was found in the individual wells as compared to the average shown by the solid bars of the graph. As can be clearly seen, the present invention provided surprising and unexpectedly significantly better cell retention than that of the prior art vacuum method. In most cases, the performance was more than 4 times better than that of the prior art.

EXAMPLE 3

Cell based apoptosis assay was performed using gravity based filtration.

Exposure of live cells to fluorochrome-labeled inhibitors of caspases (FLICAs) resulted in uptake of these reagents by apoptotic cells as FLICAs bind to activated caspases (Smolewski et al., 2001). Cells were treated with increasing concentration of well-known apoptosis inducer (Staurosporine) for 2 hours at 37° C. After induction, cells were treated with FLICA. Unbound FLICAs were removed from the non-apoptotic cells by gravity washing the cells with wash buffer 4 times. After gravity washing cells labeled with FLICAs (FAM-VAD-FMK, pan-caspases FLICA) was examined by flow cytometry.

Figure 10A:
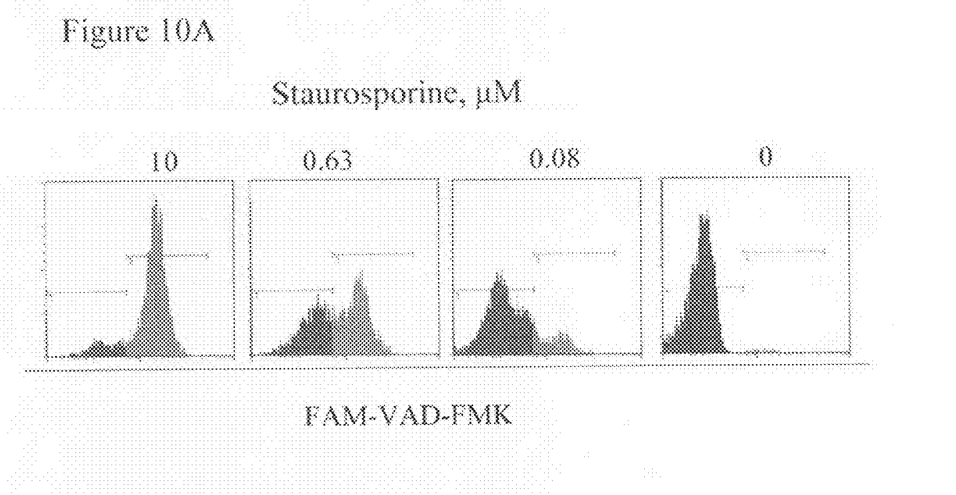
FIGS. 10A and B show data from Example 3.
Figure 10B:
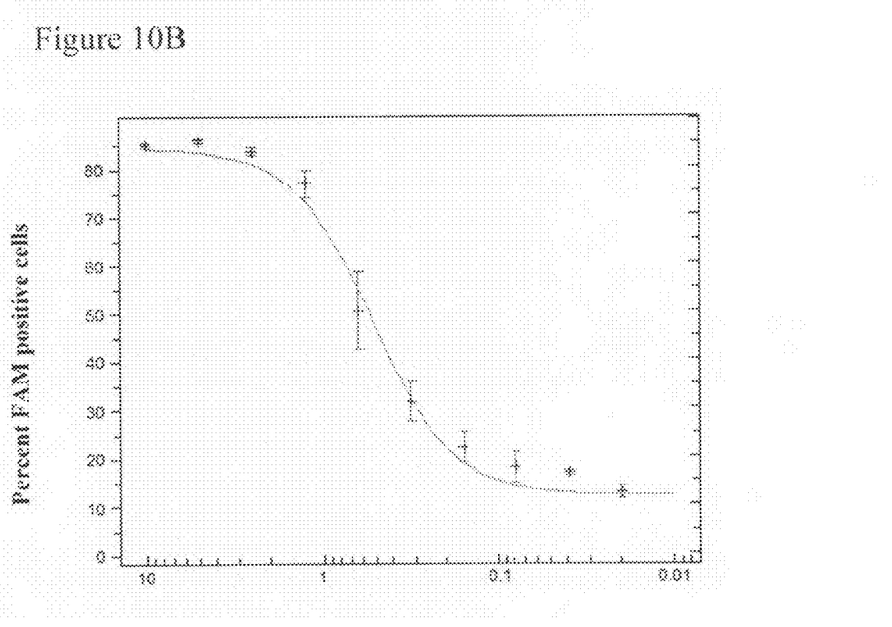

Shown in FIGS. 10A and B are flow cytometric histograms of FAM-VAD-FMK stained cells from induced (10, 0.63, 0.06 microMolar of Staurosporine) and non-induced control samples. Increase in apoptotic cell population (green populations of each histogram) as a function of increasing concentration of the inducer (Staurosporine) should be obvious to anyone trained in the art.

FIG. 10B shows numerically plotted FAM percent positive population based on flow cytometric analysis. Notice the dose response.

What is claimed is:

1. A method of detecting a target specific ligand that is bound to a target molecule to indicate the presence or absence of the target molecule comprising the steps of:
   a. selecting a cell having a selected target molecule located in a position selected from the group consisting of a cell wall or inside the cell,
   b. culturing the cell on a multiwell filter plate;
   c. contacting the cell on the multiwell filter plate with a reagent comprising a ligand for the selected target molecule in or on the cell, the ligand being selected from the group consisting of ligands having a detectable marker conjugated thereto and ligands being capable of attaching to a secondary ligand that contains a detectable marker,
   d. washing the cell with gravity flow at least one time to remove any reagent which is not bound to the selected target molecule of the cell to provide a washed cell by using sufficient fluid to achieve a head height at which filtration occurs; and
   e. detecting the presence of the ligand bound to the target molecule to indicate the presence or absence of the target molecule in or on the washed cell on the multiwall filter plate.

2. The method of claim 1 wherein the plate has a polycarbonate filter.

3. The method of claim 1 wherein the plate has a hydrophilic polycarbonate filter.

4. The method of claim 1 wherein the filter is a porous polycarbonate having a pore size of about 3 microns.

5. The method of claim 1 wherein the filter is a porous, hydrophilic, polycarbonate having a pore size of about 3 microns.

6. The method of claim 1 wherein the ligand has a detectable marker selected from the group consisting of fluorescent materials, radioactive materials, chemiluminescent, light absorbence and optical density measurements.

7. The method of claim 1 wherein the target molecule is a marker protein.

8. The method of claim 1 wherein the target molecule is a marker protein which is a cell specific marker protein.

9. The method of claim 1 wherein the target molecule is a marker protein that is a cell surface protein.

10. The method of claim 1 wherein the target molecule is a marker protein that is an intracellular protein of the cell.

11. The method of claim 1 wherein the detection for the presence of the antibody bound to the target molecule occurs in the multiwall plate by a multiwall plate reader.

12. An immunoassay method of detecting presence or absence of a target protein comprising the steps of:
   a. selecting a cell having a selected target protein located in a position selected from the group consisting of being on the cell wall or intracellular,
   b. culturing the cell on a multiwell filter plate, wherein the filter is formed of porous, hydrophilic polycarbonate having a nominal pore size of about 3 microns;

c. contacting the cell on the multiwell filter plate with at least one antibody for the selected target protein, the at least one antibody being selected from the group consisting of antibodies having a detectable marker conjugated thereto and antibodies being capable of attaching to a secondary antibody that contains a detectable marker, d. washing the cell with gravity flow at least one time to remove any antibody which is not bound to the selected target protein to provide a washed cell by using sufficient fluid to achieve a head height at which filtration occurs;

e. transferring the washed cell to a cytometer and f. detecting for the presence of the antibody bound to the target molecule to indicate the presence or absence of the target protein in or on the washed cell in the cytometer.

* * * * *

UNITED STATES PATENT AND TRADEMARK OFFICE
CERTIFICATE OF CORRECTION

PATENT NO. : 7,955,867 B2
APPLICATION NO. : 12/009508
DATED : June 7, 2011
INVENTOR(S) : Jun Y. Park Page 1 of 1

It is certified that error appears in the above-identified patent and that said Letters Patent is hereby corrected as shown below:

In column 12, line 34, in claim 1, delete "multiwall" and insert -- multiwell --, therefor.

In column 12, line 48, in claim 6, delete "absorbence" and insert -- absorbance --, therefor.

In column 12, line 59, in claim 11, delete "multiwall" and insert -- multiwell --, therefor.

In column 12, line 59, in claim 11, delete "multiwall" and insert -- multiwell --, therefor.

Signed and Sealed this
Thirteenth Day of December, 2011

David J. Kappos
*Director of the United States Patent and Trademark Office*